United States Patent [19]

Manor et al.

[11] Patent Number: 5,824,786
[45] Date of Patent: Oct. 20, 1998

[54] SYNTHESIS OF GALACTOSYLHYDROXYLYSINE

[75] Inventors: Chaim Manor, Shoreview; Jia Wei, Stillwater; Gordon D. MacFarlane, Minneapolis, all of Minn.

[73] Assignee: INCSTAR Corporation, Stillwater, Minn.

[21] Appl. No.: 706,215

[22] Filed: Aug. 30, 1996

[51] Int. Cl.$^6$ .......................... C07H 15/04; A61K 31/70
[52] U.S. Cl. ...................... 536/18.6; 536/4.1; 536/17.2; 536/17.9; 536/18.5; 536/124; 530/395
[58] Field of Search .................................. 536/4.1, 17.2, 536/18.5, 18.6, 18.7, 124, 17.9; 530/395

[56] References Cited

PUBLICATIONS

Zinn et al., *Glycoconjugates,* vol. 1 : 69–85, 1977.
Spiro, Robert, *J. Biol. Chem.,* vol. 244(3): 602–612, 1969.
Wei et al., *Journal of Bone and Mineral Research,* vol. 11 suppl. 1, p. 5409, Aug. 1996.
Askenasi et al., *Eur. J. Clin. Invest.,* vol. 6(5): 361–364, 1976.
Askenasi et al., *Method. Connect. Tissue Res.,* pp. 263–273, Joynson–Bruvvers Ltd. (Oxford, England), 1976.
Bettica et al., "Bone–Resorption Markers Galactosyl Hydroxylysine, Pyridinium Crosslinks and Hydroxproline Compared," *Clin. Chem.,* 38:2313–2318 (1992).
Bollenback et al., "The Synthesis of Aryl–D–glucopyranosiduronic Acids" *J. Am. Chem. Soc.,* 77:3310–3315 (1995).
Fieser et al., *Reagents for Organic Synthesis, vol. 1,* John Wiley & Sons, p. 192 (1969).
Ju et al., "Development of an Immunoassay for Galactosylhydroxylysine," Abstract S407, *Journal of Bone and Mineral Research,* p. S191 (Aug. 1996), from the 18th Annual Meeting of the Anerican Society for Bone and Mineral Research, Seattle, Washington, Sep. 7–12, 1996.
Moro et al., "Determination of Galactosyl Hydroxylysine in Urine as a Means for the Identification of Osteoporotic Women," *Bone and Mineral,* 3:271–276 (1988).
Moro et al., "High–Performance Liquid Chromatographic Preparation of Galactosyl–Hydroxylysine, a Specific Bone Collagen Marker," *J. Chromatography,* 490:285–292 (1989).
Moro et al., "Urinary β–1–Galactosyl–O–Hydroxylysine (GH) as a Marker of Collagen Turnover in Bone," *Calcif. Tissue Int.,* 42:87–90 (1988).

*Primary Examiner*—Marian C. Knode
*Assistant Examiner*—Howard C. Lee
*Attorney, Agent, or Firm*—Popovich & Wiles, P.A.

[57] ABSTRACT

Galactosylhydroxylysine is a terminal degradation product of the bone matrix which thus serves as biochemical marker of bone resorption. A method of synthesizing galactosylhydroxylysine is provided. Antibodies against this synthetically prepared galactosylhydroxylysine conjugated to protein carriers were raised to establish methods to measure galactosylhydroxylysine in biological fluids. The antibodies of the invention recognize native galactosylhydroxylysine and are, for example, useful in the measurement of galactosylhydroxylysine as a biochemical marker of bone resorption in biological fluids. Testing of human serum or adolescent urine resulted in dose-dependent increases in signal intensity using the method of the invention.

26 Claims, No Drawings

SYNTHESIS OF GALACTOSYLHYDROXYLYSINE

FIELD OF THE INVENTION

This invention relates to bone resorption assays. More particularly, this invention relates to the synthesis of galactosylhydroxylysine, antibodies to galactosylhydroxylysine, and a method of assaying for galactosylhydroxylysine.

BACKGROUND OF THE INVENTION

Biochemical markers of bone resorption provide the potential for the detection of small changes in bone metabolism prior to observable changes by x-ray methods. Several collagen degradation products have been examined as potential biochemical markers. Galactosylhydroxylysine, a terminal metabolite in human bone collagen degradation, has been identified by Moro et al. as a potential bone resorption marker (Moro et al., *Calcif Tissue Int.*, 42:87–90 (1988); Moro et al., *Bone and Mineral*, 3:271–276 (1988)). Galactosylhydroxylysine has been shown to correlate well with established markers of bone resorption, and may discriminate normal from mildly increased bone resorption states with low population variability (Bettica et al., *Clin. Chem.* 38:2313–2318 (1992)). Present methods (high pressure liquid chromatography, HPLC) for the isolation and purification of galactosylhydroxylysine require chemical modification of the molecule. Moreover, preparation of a commercial assay for galactosylhydroxylysine has been hindered by the inability to isolate large quantities of native material necessary for the production and screening of immunogenic conjugates.

Methods for the HPLC analysis of galactosylhydroxylysine in urine have been developed by Moro et al. (Moro et al., *J. Chromatography*, 490:285–292 (1989)). Though these HPLC methods have provided important data demonstrating the clinical utility of galactosylhydroxylysine as a marker of bone resorption, their use in a routine clinical setting is severely limited. In order to solve this problem, the present invention provides an immunoassay, which may be supplied in kit form, for the detection of galactosylhydroxylysine that utilizes antibodies to galactosylhydroxylysine and galactosylhydroxylysine conjugate. Methods of generating high yields of galactosylhydroxylysine, galactosylhydroxylysine conjugates, and antibodies to galactosylhydroxylysine are also disclosed herein.

SUMMARY OF THE INVENTION

The invention provides a method of making galactosylhydroxylysine comprising:

(a) reacting a compound of the formula I

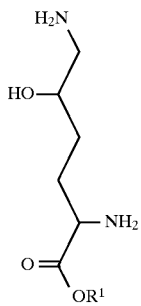

wherein $R^1$ is H or —$CH_3$, with a compound that provides an amino-protecting group, $P^A$, and, if $R^1$ is H, a compound that provides a carboxyl-protecting group, $P^C$, to give a compound of the formula II

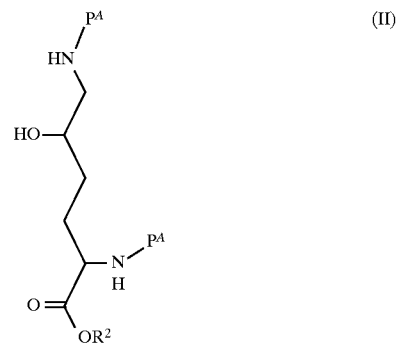

wherein $R^2$ is $P^C$ or —$CH_3$;

(b) reacting the compound of the formula II above with a compound of the formula III

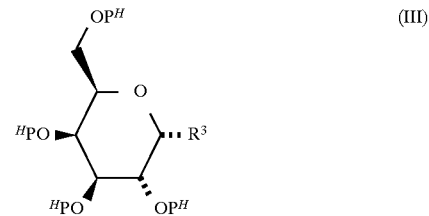

wherein pH is a hydroxyl-protecting group and $R^3$ is selected from Br, Cl, I, or —O-toluene sulfonate; to give a compound of the formula IV

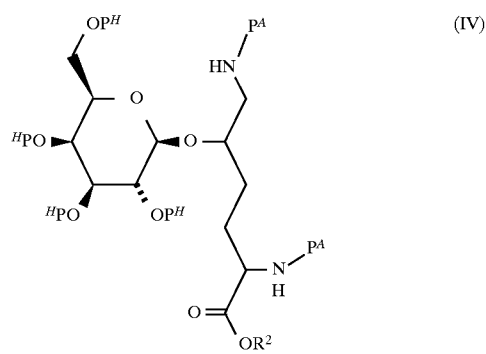

(c) reacting the compound of the formula IV with a compound that removes the amino-protecting groups, $P^A$, and replaces them with H; with a compound that removes the carboxyl-protecting group, $P^C$, or the original —$CH_3$ group at the same position in the compound of formula I, and replaces it with H; and with a compound that removes the hydroxyl-protecting groups, $p^H$, and replaces them with H; to give galactosylhydroxylysine (V)

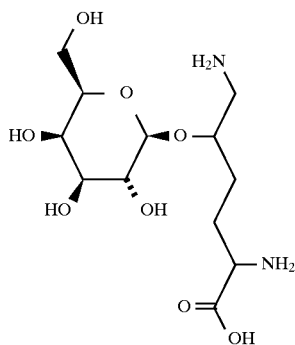

(V)

The invention also provides a galactosylhydroxylysine conjugate comprising galactosylhydroxylysine and a protein carrier. The invention provides monoclonal antibodies and polyclonal antibodies which specifically bind to galactosylhydroxylysine.

The invention provides a method of assaying for galactosylhydroxylysine in a sample comprising: (a) contacting with the sample a specific binding agent that is capable of binding to galactosylhydroxylysine; (b) measuring the amount of binding of the specific binding agent to the galactosylhydroxylysine in the sample; and (c) correlating the amount of binding of the specific binding agent to the galactosylhydroxylysine to the amount of galactosylhydroxylysine in the sample.

Additional features and advantages of the invention are set forth in the description which follows and in part will be apparent from the description. The objectives and other advantages of the invention will be realized and attained by the synthesis of galactosylhydroxylysine, the synthesis of galactosylhydroxylysine conjugates, antibodies to galactosylhydroxylysine, and method of assaying for galactosylhydroxylysine as particularly pointed out in the written description and claims.

It is to be understood that both the foregoing general description and the following detailed description are exemplary and explanatory and are intended to provide further explanation of the invention as claimed.

DETAILED DESCRIPTION OF THE INVENTION

The invention provides a method of making galactosylhydroxylysine as described above. In a preferred embodiment $R^1$ is H. In another preferred embodiment, $p^A$ is selected from a carbamate group, amide group, imide group, N-alkyl amine, N-alkyl imine, N-alkenyl amine, N-alkenyl imine, N-aryl amine, or N-aryl imine. $p^A$ may be selected from carbamate groups such as t-butoxycarbonyl (t-Boc) as well as other alkyl, alkenyl, aryl carbamates and their substituted derivatives, 9-fluorenylmethylcarbonyl (Fmoc) and substituted Fmoc; amide and imide groups such as N-acetyl and its derivatives, N-formyl and other N-aliphatic acid derivatives; N-benzoyl and other N-aromatic acid derivatives; and N-phthlimide and other cyclic 5- or 6-membered ring derivatives; and N-alkyl, N-alkenyl, and N-aryl amine and imine groups such as N-methyl, methylene, methine and their derivatives and N-allyl and its derivatives; and other N-heteroatom derivatives such as N-metal and N-nonmetal derivatives. More preferably, $p^A$ is selected from a carbamate group; in a preferred embodiment $p^A$ is 9-fluorenylmethylcarbonyl. In another preferred embodiment, the compound that provides an amino-protecting group is 9-fluorenylmethyl chloroformate. To protect an amino group, the substrate is reacted with a protecting group in a suitable solvent with or without a catalyst under predetermined conditions for a designated period. After the reaction is complete, the solvent is removed and the crude product is isolated and purified.

In a preferred embodiment of the invention, $P^C$ is selected from methyl, ethyl, $C_3$ to $C_{12}$ alkyl, or silyl; more preferably, $P^C$ is selected from $C_1$ to $C_{12}$ alkyl. $P^C$ may be substituted methyl, ethyl, and other alkyl groups and substituted silyl and other heteroatom groups. In a preferred embodiment, $P^C$ is —$CH_3$. In another preferred embodiment, the compound that provides the carboxyl-protecting group is diazomethane. To protect a carboxyl group, the substrate is reacted with a protecting group in a suitable solvent with or without a catalyst under predetermined conditions for a designated period. After the reaction is complete, the solvent is removed and the crude product is isolated and purified.

In one embodiment $p^H$ is selected from —$COCH_3$, —COPh (benzoyl), and other ester forming groups, $SiMe_3$ (trimethylsilyl) and other silyl derivatives; in a preferred embodiment $p^H$ is —$COCH_3$. In a preferred embodiment, $R^3$ is Br. $R^3$ may also be any other appropriate heteroatom or a derivative thereof.

The compound that removes the amino-protecting group may be selected from an organic base or inorganic base or a solution thereof with a pH greater than 10; or an organic or inorganic acid or a solution thereof with a pH less than 2. In one embodiment, the compound that removes the amino-protecting group is selected from ammonia, piperidine, morpholine, a secondary or tertiary amine, or ammonium salt. In a preferred embodiment, the compound that removes the amino-protecting group is piperidine.

The compound that removes the carboxyl-protecting group may be selected from NaOH, $K_2CO_3$, other inorganic bases, organic bases or an enzyme such as Pig Liver Esterase. In a preferred embodiment, the compound that removes the carboxyl-protecting group is NaOH. In another preferred embodiment, the compound that removes the hydroxyl-protecting group is the same compound that removes the carboxyl-protecting group. In one embodiment, the compound that removes the hydroxyl-protecting group is NaOH, triethyl amine, or other organic or inorganic bases. In a preferred embodiment, the compound that removes the hydroxyl-protecting group is NaOH. Appropriate solvents for the deprotection reactions include N,N'-dimethylfonnamide (DMF), methanol, ethanol, and other alcoholic solvents, 1,4-dioxane and other cyclic ethers.

In one embodiment, a catalyst is present in step (b). The catalyst may be selected from $Hg(CN)_2$, $K_2CO_3$, $AgNO_3$, $Ag2CO_3$, $HgBr_2/Hg(CN)_2$, or HgO. In addition, other silver, mercuric, and other heavy metal compounds may be used. In a preferred embodiment, the catalyst is $Hg(CN)_2$. Appropriate solvents for step (b) include anhydrous toluene, nitromethane, 1,2-dichloroethane, acetone, chloroform, benzene, xylenes, and acetonitrile. Appropriate temperatures for conducting each of the steps of the synthesis of galactosylhydroxylysine are known in the art.

In a preferred embodiment, step (a) is two separate steps, a first step of reacting the compound of formula I with a compound providing an amino-protecting group, $p^A$, and a second step of reacting the product of the first step with the compound providing a carboxyl-protecting group, $p^C$.

The invention provides a method of making galactosylhydroxylysine comprising:

(a) reacting a compound of the formula I

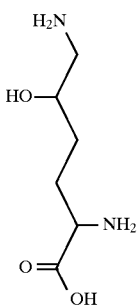

with 9-fluorenylmethyl chloroformate to provide an aminoprotecting group, —Fmoc, and then reacting the amino-protected compound with diazomethane to provide a carboxyl-protecting group, —CH₃, to give a compound of the formula II

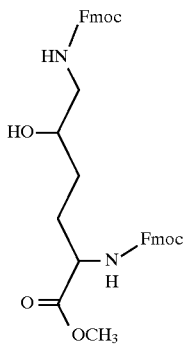

(b) reacting the compound of the formula II above with a compound of the formula III

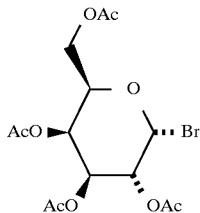

to give a compound of the formula IV

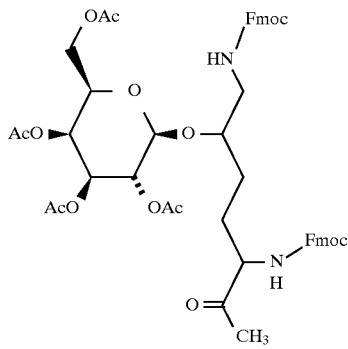

(c) reacting the compound of the formula IV with piperidine to remove the amino-protecting groups, —Fmoc, and replace them with H; with NaOH to remove the carboxyl-protecting group, —CH₃, and replace it with H; and with NaOH to remove the hydroxyl-protecting groups, —Ac; to give galactosylhydroxylysine (V)

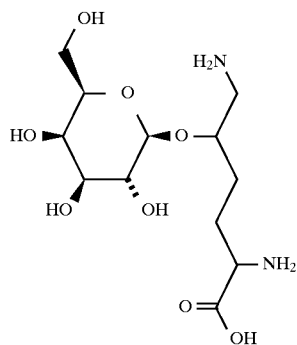

The invention provides a galactosylhydroxylysine conjugate comprising galactosylhydroxylysine and a protein carrier. In one embodiment the protein carrier is selected from horse-radish-peroxidase, bovine serum albumin, thyroglobulin, alkaline phosphatase, and keyhole lympet haemocyanin. In a preferred embodiment, the protein carrier is selected from horse-radish-peroxidase, bovine serum albumin, or thyroglobulin.

The invention provides a method of assaying for galactosylhydroxylysine in a sample comprising: (a) contacting with the sample a specific binding agent that is capable of binding to galactosylhydroxylysine; (b) measuring the amount of binding of the specific binding agent to the galactosylhydroxylysine in the sample; and (c) correlating the amount of binding of the specific binding agent to the galactosylhydroxylysine to the amount of galactosylhydroxylysine in the sample. The specific binding agent may be a polyclonal or monoclonal antibody.

The invention provides a monoclonal antibody which specifically binds to galactosylhydroxylysine and a polyclonal antibody which specifically binds to galactosylhydroxylysine.

In the preferred embodiment of the method of assaying for galactosylhydroxylysine, galactosylhydroxylysine conjugated to BSA is adsorbed onto the surface of a reaction well. This attaches the galactosylhydroxylysine to the reactor well sufficient to remain attached throughout the conditions of the assay. In conducting the assay, the sample containing or suspected of containing the galactosylhydroxylysine is added to the above prepared reaction well along with a known amount of an antibody specific to galactosylhydroxylysine. This mixture is allowed to react under incubation conditions, resulting in competition of the galactosylhydroxylysine in the sample with the galactosylhydroxylysine-BSA conjugate attached to well for the antibody. Following incubation, the reaction well is washed to remove unbound material, resulting in some of the initial amount of antibody being bound to the galactosylhydroxylysine-BSA conjugate attached to the well. A second antibody specific to the first antibody and having a signal generator attached is incubated with the contents of the well, resulting in a second antibody being bound inside the reactor well. After washing to remove unbound material, the signal generator is measured. The signal will correlate inversely with the amount of galactosylhydroxylysine in the sample.

As an alternative to the foregoing, a double antibody competitive assay may be used. In this format, for example, the sample may be reacted with an antibody specific to galactosylhydroxylysine and galactosylhydroxylysine labeled with a signal generator. Following the reaction incubation, a second antibody specific to the first antibody may be incubated with product of the first incubation to cause precipitation of the double antibody galactosylhydroxylysine complex, which may be augmented by centrifugation. Following separation of precipitated material from the supernatant, the signal generated by the precipitated material will correspond inversely with amount of galactosylhydroxylysine in the sample.

Other assays involving a competitive format, known to the art, may be employed. The signal generator may be anything that allows detection according to known means, including without limitation, chemiluminescence, luminescence, an enzyme, radioiodine, etc. The antibodies, whether the first or second (if applicable), may be polyclonal or monoclonal. Antibodies may be substituted by any specific binding agent, including without limitation, an antibody fragment or construct (containing exogenous polypeptide sequence or chemical materials) containing at least a paratope, a purified receptor or receptor fragment or construct or a synthetic polypeptide capable of such specific binding.

EXAMPLE 1

Synthesis of GHYL (galactosylhydroxylysine)

A four-step procedure was employed to synthesize racemic GHYL. Generally, δ-Hydroxyl-DL-lysine was first treated with 9-fluorenylmethyl chloroformate (Fmoc-Cl) in a standard fashion to produce Fmoc protected lysine. This Fmoc protected lysine was then methylated with diazomethane. The amino and carboxyl protected δ-hydroxy-DL-lysine was then catalytically coupled with acetobromo galactose at elevated temperature. The structure of the product was confirmed by nuclear magnetic resonance (NMR) and mass spectroscopy (MS). Finally, the fully protected GHYL was de-blocked with piperidine and sodium hydroxide, resulting in high yield of GHYL. The following discussion describes this four-step procedure in more detail.

A. Preparation of N,N'-Di-(9-Fluorenylmethoxycarbonol-5-Hydroxy-DL-lysine (also N,N'-Di-Fmoc-5-Hydroxy-DL-lysine)

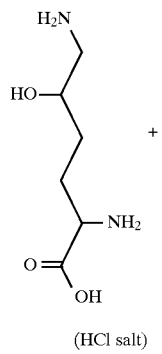

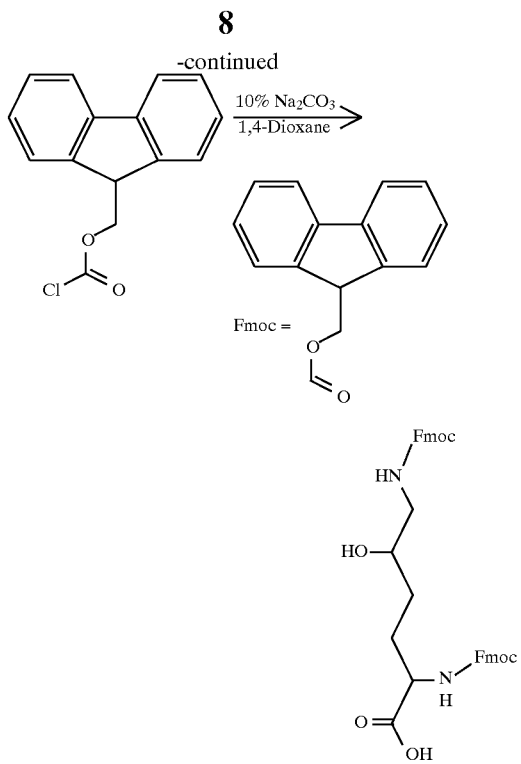

A solution of 9-fluorenylymethyl chloroformate (Fmoc-Cl) (5.69 g, 0.022 mol) in 60 ml of anhydrous 1,4-dioxane was added, over 30 minutes with stirring, to a solution of 5-hydroxy-DL-lysine hydrochloride (1.99 g, 0.01 mol) in 65 ml of 10% aqueous sodium carbonate cooled with an ice-water bath. The reaction mixture was stirred at 0°–4° C. for 2 hours and room temperature overnight. The resulting milky suspension was poured into 500 ml of water and extracted with diethyl ether (100 ml) five times. The aqueous layer was cooled in an ice-water bath and acidified to pH 3 with concentrated hydrochloric acid. The precipitated product was extracted with ethyl acetate (100 ml) four times and the combined organic phase was washed with 100 ml of water, 100 ml of saturated sodium chloride solution, and dried over anhydrous magnesium sulfate. Evaporation of the solvent afforded 6.1 g white solid product in quantitative yield. MS (Fab): 607 $[M+H]^+$, 605 $[M—H]^+$. IR (film, $cm^-$): 1716 (Fmoc C=O).

B. Preparation of N,N'-Di-(9-Fluorenylmethoxycarbonyl)-5-Hydroxy-DL-lysine Methyl Ester (also N,N'-Di-Fmoc-5-Hydroxy-DL-lysine Methyl Ester)

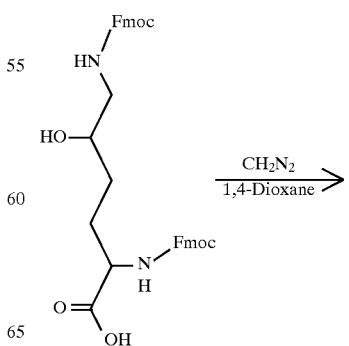

-continued

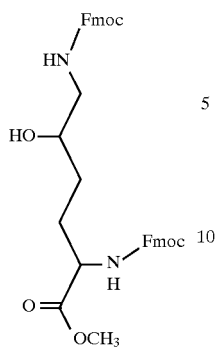

To a solution of N,N'-Di-(9-fluorenylmethoxycarbonyl)-5-hydroxy-DL-lysine (2.0 g, 0.0033 mol) in 20 ml of anhydrous 1,4-dioxane was added, dropwise with stirring, an etherate solution of diazomethane until a light yellow color persisted. (The etherate solution of diazomethane was prepared with 1.0 g of 1-methyl-3-nitro-1-nitrosoguanidine in 5 ml of 40% sodium hydroxide and 30 ml of diethyl ether by a standard method described in Fieser et al., *Reagents for Organic Synthesis*, Vol. 1, John Wiley & Sons, Inc., 1969, p. 192. The reaction was stirred at ambient temperature for one hour and the solvent was evaporated to give 2.1 g of the product in quantitative yield.

C. Coupling of N,N'-Di-(9-Fluorenylmethoxycarbonyl-5-Hydroxy-DL-lysine Methyl Ester And Acetobromo Galactose

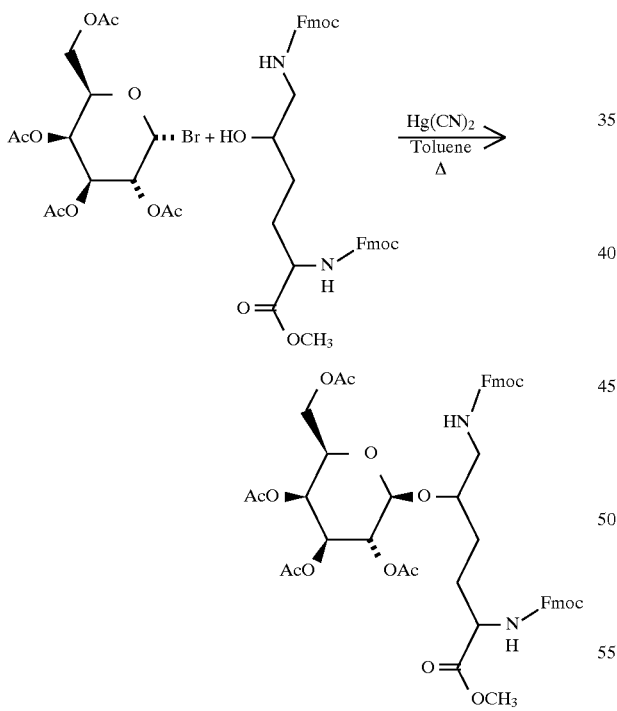

To a solution of acetobromo galactose (0.65 g, 0.0016 mol, acetobromo galactose is available from Sigma Chemical Co., St. Louis, Mo., and may be made by the method described in Bollenback et al., *J. Am. Chem. Soc.*, 77:3310 (1955)) and N,N'-Di-(9-fluorenylmethoxycarbonyl)-5-hydroxy-DL-lysine methyl ester (1.0 g, 0.0016 mol) in 10 ml of anhydrous toluene was added mercury cyanide (0.49 g, 0.0019 mol). The reaction mixture was then heated to 75° C. in darkness for 24 hours. After cooling to room temperature, the off-white slurry was filtered and the solid was washed with 1 ml of fresh toluene. The filtrate was evaporated and redissolved in 1.25% methanol in chloroform and purified by column chromatography (110 g silica gel, 1.25% methanol in chloroform) to give 1.5 g of the product (yield: 96%). MS (Fab, m/z): 951.3 [M+H]$^+$. IR (NaCl, film): 1749 (acetyl C=O), 1722 (Fmoc C=O).

D. Preparation Of Galactosylhydroxylysine (GHYL)

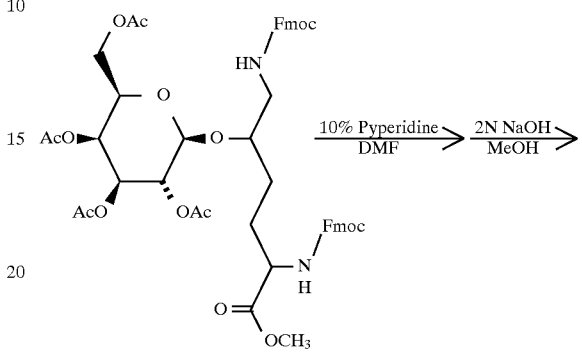

The fully protected GHYL (0.88 g, 0.93 mmol) was stirred at room temperature in 5 ml of 10% piperidine in DMF for 1.5 hours. The solution was diluted with 30 ml of water and extracted with ethyl acetate (15 ml) four times. The aqueous phase was evaporated to dryness and the residue was suspended in 5 ml of 1:1 NaOH (40%):methanol and stirred at room temperature overnight. It was then neutralized with concentrated HCl and evaporated to dryness. The crude product was extracted with anhydrous methanol and purified by column chromatography (silica gel, 30 g, 80% methanol) to give 0.64 g product. MS(Fab, m/z): 342.1 [M+H]$^+$, 346.1 [M+Na]$^+$.

EXAMPLE 2

Synthesis of GHYL-HRP Conjugate

This conjugate was prepared by cross-linking GHYL and horse-radish-peroxidase (HRP) through disuccinimidyl suberate (DSS). Specifically, a solution of GHYL (1.2 mg, 3.75 mmol) in 0.5 ml of 0.1M sodium acetate (pH=6) was added to a solution of disuccinimidyl suberate (DSS, 1.5 mg, 4.13 umol) in 0.5 ml of DMF at 0° C. The reaction was stirred at 0° C. for 40 minutes. Then a solution of horse-radish peroxidase (HRP, 15 mg, 0.375 umol) in 1 ml of 0.5% sodium bicarbonate was added. After stirring at room temperature for 5 hours, the crude conjugate was dialyzed in phosphate buffered saline (PBS).

The GHYL-HRP conjugate has the structure:

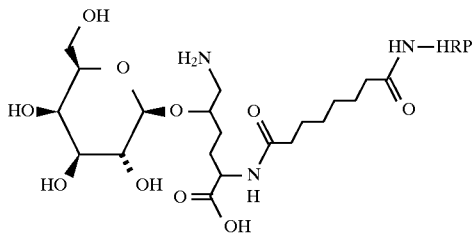

EXAMPLE 3

Synthesis of GHYL-BSA Conjugate

This conjugate was prepared according to the method described in Example 2 by cross-linking GHYL and bovine serum albumin (BSA) through disuccinimidyl suberate (DSS).

The GHYL-BSA conjugate has the structure:

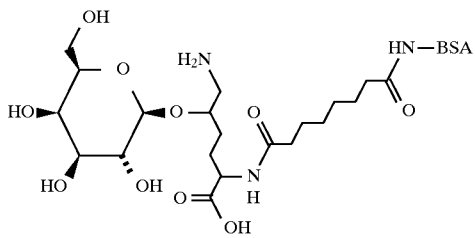

EXAMPLE 4

Synthesis of GHYL-Tg Conjugate

This conjugate was prepared according to the method described in Example 2 by cross-linking GHYL and thyroglobulin (Tg) through disuccinimidyl suberate (DSS).

The GHYL-Tg conjugate has the structure:

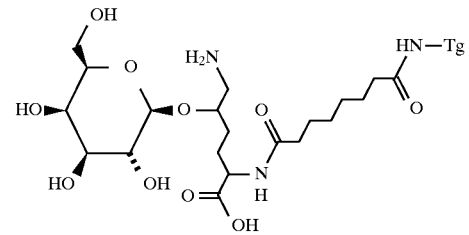

EXAMPLE 5

Preparation of Rabbit Polyclonal Antibody to GHYL

The GHYL-thyroglobulin conjugate was used as an immunogen for rabbit polyclonal antisera. Six rabbits were injected (subcutaneous, SC) with 100 µg of GHYL-thryroglobulin conjugate in Complete Freund's adjuvant. Three booster injections (SC) of 5–10 µg of conjugate in Incomplete Freund's adjuvant were given at two to four week intervals. Sera was screened one week after each booster injection. All six rabbits exhibited anti-GHYL titers in excess of 1 to 1 million. The GHYL-BSA conjugate was used to screen the antisera.

EXAMPLE 6

Preparation of Monoclonal Antibody to GHYL

GHYL-thyroglobulin conjugates were used as immunogens to raise monoclonal antibodies in BALB/c mice. BALB/c mice were initially immunized (subcutaneous, SC) with 100 µg of GHYL-thryroglobulin conjugate in Complete Freund's adjuvant. Three booster injections (SC) of 5–10 µg of conjugate in Incomplete Freund's adjuvant were given at two to four week intervals. Sera was screened one week after each booster injection. Selected mice were given an additional booster injection (intraperitoneal, IP) of 100 µg of conjugate in 0.5 ml PBS three days prior to fusion.

Spleen cells were isolated from mice and were fused to the non-producer myeloma X63-Ag8.653 variant cell line (available from American Type Culture Collection, Rockville, Md.).Fusions were performed according to the following procedure. Feeder layers were prepared the day before the fusion. $1.6 \times 10^7$ mouse peritoneal cells were collected from two unimmunized BALB/c mice and the cells were plated to sixteen 96-well plates at $1.0 \times 10^4$ cells per well. On the day of fusion, $3.4 \times 10^8$ spleen cells (derived from one immunized mouse) and $9.2 \times 10^7$ X63-Ag8.653 cells were washed with serum-free IMDM (Iscove's Modified Dulvecco's Medium) medium and mixed in a 50 ml conical tube. The tube was then filled up with IMDM medium and centrifuged at 200 g for 7 minutes. All the supernatant was aspirated completely. A total of 1 ml warm PEG-solution (2.5 g PEG in 2.25 ml IMDM and 0.25 ml DMSO; PEG, M. W. 4000, EM Science, Cat. No. 9727-2) was added dropwise to the pellet under gentle agitation over a period of 1 minute at 37° C. After 90 seconds of incubation at 37° C. water bath, 1 ml warm IMDM medium was added in 1 minute and an additional 20 mLs of IMDM was added in 4 minutes. The mixture was centrifuged at 200 g for 10 minutes, after which the supernatant was totally discarded. The fused mixture was resuspended in IMDM medium supplemented with 20% fetal bovine serum, 4.0 mM L-glutamine, 100 ug.h.nL streptomycin sulfate and 100 ug/mL penicillin, 0.05 mM β-mercaptoethanol, 1.0 mM sodium pyruvate, 6% LPS activated P388 supernatant, 0.0036 mg/mL insulin and 20–50% conditioned medium (myeloma cells spent medium). The fused cell suspension was distributed over the feeder-layers. The plates were incubated in a 37° C., 7.5% $CO_2$ incubator.

The resulting hybridomas were screened against a GHYL-BSA conjugate in a competitive enzyme-linked immunosorbent assay (ELISA). GHYL-BSA was adsorbed to the microtiter plate. Microtiter plates were coated overnight with GHYL-BSA (0.5 ug/well in 50 mM carbonate buffer), washed three times with PBS and stored wet at 4° C. For screening assays, monoclonal antibody was then added to the wells and incubated for one hour. After washing, goat anti-mouse IgG conjugated to HRP (available from Kierkegard & Perry Laboratories, Gaithersburg, Md.) was added and incubated for 30 minutes. The plate was washed, chromogen (TMB, available from Intergen, Purchase, N.Y.) was added and incubated for 30 minutes, then stopped with 2N sulfuric acid and read at 450 nm. Positive hybridomas were further characterized by suppression assays in which free GHYL or potential cross-reactants were added with the monoclonal antibody. Potential cross-reactants were tested at 60 mM in buffer.

Twenty-eight positive clones were subcloned by a limiting dilution method. HT-containing (hypoxanthine and thymidine-containing) IMDM was used for subcloning. All twenty-eight monoclones were rescreened by both screening methods and twenty-one clones retained the ability of secreting antibodies against GHYL-BSA conjugate. Four positive clones, given the designations 1C7C7, 15A2H11, 9B3C8, and 8E10E7, were selected for ascites production.

For ascites production, each of the four clones was transplanted in a dose of $2 \times 10^6$ cells/0.5 mL PBS/mouse into the peritoneal cavities of three female IRCF1 mice, which had been treated with intraperitoneal pristane injection six days before the hybridoma inoculation. The dose of pristane was 0.5 mL/mouse. After 10–14 days, the ascitic fluids were collected. About 8–24 mL of ascites fluid was obtained from each mouse group.

The ascites from each of the four clones were characterized by suppression assays in which free GHYL or potential cross-reactants were added with the monoclonal antibody. Potential cross-reactants were tested at 60 mM in buffer (PBS). Results of these assays are shown in Tables 1 and 2. The four clones were screened for cross-reactivity to lysine, hydroxylysine, glucose, galactose, lactose, and glucosyl-galactosylhydroxylysine. Three of four clones show limited suppression when evaluated with these potential cross-reactants. Two clones showed less than 10% signal suppression to all compounds tested at concentrations from 30 mM to 60 mM.

The procedure of the suppression assay was as follows. To each well was added 50 ul of ascites diluted 1:50 (clones 1C7C7; 9B3C8; 8E1OE7) or 1:100 (clone 15A2H1 1). Fifty uL of suppressor sample (hydroxylysine, lysine, galactose, glucose, lactose, or glucosyl-galactosylhydroxylysine at 30 or 60 mM) or buffer blank was added to wells in duplicate. The plate was covered and incubated at room temperature on a shaker at 700 rpm for one hour. The plate was washed three cycles with wash solution (PBS-BSA with 0.2% Tween 20 and 0.05% ProClin). Fifty uL of goat anti-mouse IgG (available from Kierkegard & Perry Laboratories, Gaithersburg, Md.) diluted 1:1000 with PBS that contains 1% BSA, 0.2% Tween 20, and 0.05% ProClin by weight) then was added. All percentages herein are percentages by weight. The plate was covered and incubated at room temperature on a shaker at 700 rpm for 30 minutes. The plate was washed three times with wash solution. One hundred uL of chromogen solution (TMB, purchased from Intergen, Purchase, N.Y.) was added and the plate was incubated at 700 rpm for thirty minutes. Finally, 200 ul of stop solution (2N sulfuric acid) was added and the plate was read at 450 nm.

TABLE 1

| | Hydroxylysine | | Lysine | | Galactose | |
|---|---|---|---|---|---|---|
| | 30 | 60 | 30 | 60 | 30 | 60 |
| 1C7C7 | 2.230 | 2.587 | 2.704 | 2.608 | 2.782 | 2.723 |
| 15A2H11 | 1.455 | 0.609 | 1.063 | 0.726 | 1.667 | 1.535 |

TABLE 1-continued

| | | | | | | |
|---|---|---|---|---|---|---|
| 9B3C8 | 1.776 | 1.770 | 1.998 | 2.05 | 2.163 | 2.097 |
| 8E10B7 | 2.682 | 2.907 | 2.990 | 2.966 | 3.162 | 3.15 |

| | Glucose | | Lactose | | Glucosyl-galactosyl hydroxylysine | | |
|---|---|---|---|---|---|---|---|
| | 30 | 60 | 30 | 60 | 30 | 60 | Blank |
| 1C7C7 | 2.514 | 2.556 | 2.678 | 2.612 | N/A | N/A | 2.714 |
| 15A2H11 | 1.610 | 1.728 | 1.386 | 1.164 | N/A | N/A | 1.706 |
| 9B3C8 | 2.042 | 2.013 | 1.906 | 1.921 | 3.652* | 3.491* | 1.954 |
| 8E10E7 | 3.200 | 3.171 | 3.020 | 2.845 | > | > | 3.125 |

*Assay Blank: 2.632

TABLE 2

Percent Suppression by 60 mmol Inhibitor

| | Blank | Hydroxy-lysine | Lysine | Galactose | Glucose | Lactose | Glucosyl-galactosyl-hydroxylysine |
|---|---|---|---|---|---|---|---|
| 1C7C7 | 0 | 5 | 4 | 0 | 6 | 4 | N/A |
| 15A2H11 | 0 | 64 | 57 | 10 | 0 | 32 | N/A |
| 9B3C8 | 0 | 9 | 0 | 0 | 0 | 2 | 0 |
| 8E10E7 | 0 | 7 | 5 | 0 | 0 | 9 | 0 |

EXAMPLE 7

Immunoassay for GHYL

An assay similar to the one in Example 6 used to screen the four clones for cross-reactivity was used to characterize human serum and adolescent urine.

The procedure of the assay was as follows. To the well was added 50 ul of serum or urine or dilution to be tested. Fifty uL of buffer blank was added to the well and ascites diluted 1:50 or 1:100. The plate was covered and incubated at room temperature on a shaker at 700 rpm for one hour. The plate was washed three cycles with wash solution (PBS-BSA with 0.2% Tween 20 and 0.05% ProClin). Fifty uL of goat anti-mouse IgG (available from Kierkegard & Perry Laboratories, Gaithersburg, Md.) diluted 1:1000 with PBS that contains 1% BSA, 0.2% Tween 20, and 0.05% ProClin by weight) then was added. The plate was covered and incubated at room temperature on a shaker at 700 rpm for 30 minutes. The plate was washed three times with wash solution. One hundred uL of chromogen solution (TMB, purchased from Intergen, Purchase, N.Y.) was added and the plate was incubated at 700 rpm for thirty minutes. Finally, 200 ul of stop solution (2N sulfuric acid) was added and the plate was read at 450 nm.

Initial serial dilutions of human serum (to 1:10) or adolescent urines (to 1:10) resulted in a dose dependent increase in signal intensity, indicating the suitability of the antibodies and conjugates for assays.

Results are presented in Table 3.

TABLE 3

| | Dose Dependent Absorbance Increases in Response to Serum or Urine Dilutions | | | | | |
| --- | --- | --- | --- | --- | --- | --- |
| | SERUM | | | URINE | | |
| | Neat | 1:3 | 1:10 | Neat | 1:5 | 1:10 |
| 9B3C8 | 1.521 | 2.090 | 2.797 | 1.326 | 1.358 | 2.562 |
| 8E10E7 | 2.222 | 2.517 | 3.009 | 0.956 | 3.387 | 3.350 |

The above description is provided for the purpose of describing embodiments of the invention and are not intended to limit the scope of the invention in any way. It will be apparent to those skilled in the art that various modifications and variations can be made in the synthesis of galactosylhydroxylysine, the synthesis of galactosylhydroxylysine conjugates, antibodies to galactosylhydroxylysine, and method of assaying for galactosylhydroxylysine without departing from the spirit or scope of the invention. Thus, it is intended that the present invention cover the modifications and variations of this invention provided they come within the scope of the appended claims and their equivalents.

What is claimed is:

1. A method of making galactosylhydroxylysine comprising:

(a) reacting a compound of the formula I

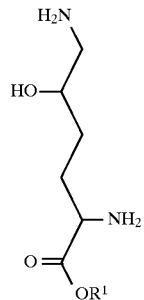

wherein $R^1$ is H or —$CH_3$, with a compound that provides an amino-protecting group, $P^A$, and, if $R^1$ is H, a compound that provides a carboxyl-protecting group, $P^C$, to give a compound of the formula II

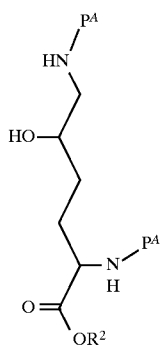

wherein $R^2$ is $P^C$ or —$CH_3$;

(b) reacting the compound of the formula II above with a compound of the formula III

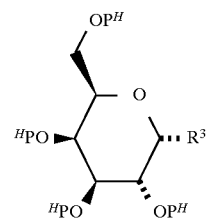

wherein $P^H$ is a hydroxyl-protecting group and $R^3$ is selected from Br, Cl, I, or —O-toluene sulfonate; to give a compound of the formula IV

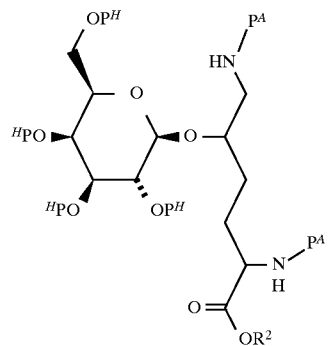

(c) reacting the compound of the formula IV with a compound that removes the amino-protecting groups, $P^A$, and replaces them with H; with a compound that removes the carboxyl-protecting group, $P^C$, or the original —$CH_3$ group at the same position in the compound of formula I, and replaces it with H; and with a compound that removes the hydroxyl-protecting groups, $P^H$, and replaces them with H; to give galactosylhydroxylysine (V)

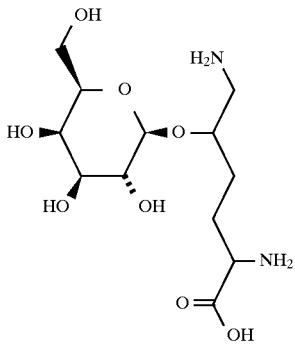

2. The method of claim 1, wherein $R^1$ is H.

3. The method of claim 1, wherein $P^A$ is selected from a carbamate group, amide group, imide group, N-alkyl amine, N-alkyl imine, N-alkenyl amine, N-alkenyl imine, N-aryl amine, or N-aryl imine.

4. The method of claim 1, wherein $P^A$ is selected from a carbamate group.

5. The method of claim 1, wherein $P^A$ is 9-fluorenylmethylcarbonyl.

6. The method of claim 1, wherein the compound that provides an amino-protecting group is 9-fluorenylmethyl chloroformate.

7. The method of claim 1, wherein $P^C$ is selected from methyl, ethyl, $C_3$ to $C_{12}$ alkyl, or silyl.

8. The method of claim 1, wherein $P^C$ is selected from $C_1$ to $C_{12}$ alkyl.

9. The method of claim 1, wherein $P^C$ is —$CH_3$.

10. The method of claim 1, wherein the compound that provides the carboxyl-protecting group is diazomethane.

11. The method of claim 1, wherein $P^H$ is selected from —COCH$_3$, —COPh, and other ester forming groups, SiMe$_3$, and other silyl derivatives.

12. The method of claim 1, wherein $P^H$ is —COCH$_3$.

13. The method of claim 1, wherein $R^3$ is Br.

14. The method of claim 1, wherein the compound that removes the amino-protecting group is selected from an organic base or inorganic base or a solution thereof with a pH greater than 10; or an organic or inorganic acid or a solution thereof with a pH less than 2.

15. The method of claim 1, wherein the compound that removes the amino-protecting group is selected from ammonia, piperidine, morpholine, a secondary or tertiary amine, or ammonium salt.

16. The method of claim 1, wherein the compound that removes the amino-protecting group is piperidine.

17. The method of claim 1, wherein the compound that removes the carboxyl-protecting group is selected from NaOH, K$_2$CO$_3$, other inorganic bases, organic bases or an enzyme.

18. The method of claim 1, wherein the compound that removes the carboxyl-protecting group is NaOH.

19. The method of claim 1, wherein the compound that removes the hydroxyl-protecting group is the same compound that removes the carboxyl-protecting group.

20. The method of claim 1, wherein the compound that removes the hydroxyl-protecting group is NaOH, triethyl amine, or other organic or inorganic bases.

21. The method of claim 1, wherein the compound that removes the hydroxyl-protecting group is NaOH.

22. The method of claim 1, wherein a catalyst is present in step (b).

23. The method of claim 22, wherein the catalyst is selected from Hg(CN)$_2$, K$_2$CO$_3$, AgNO3, Ag$_2$CO$_3$, HgBr$_2$/Hg(CN)$_2$, HgBr$_2$/HgO or HgO.

24. The method of claim 22, wherein the catalyst is Hg(CN)$_2$.

25. The method of claim 1, wherein step (a) is two separate steps, a first step of reacting the compound of formula I with a compound providing an amino-protecting group, $P^A$, and a second step of reacting the product of the first step with the compound providing a carboxyl-protecting group, $P^C$.

26. A method of making galactosylhydroxylysine comprising:

(a) reacting a compound of the formula I

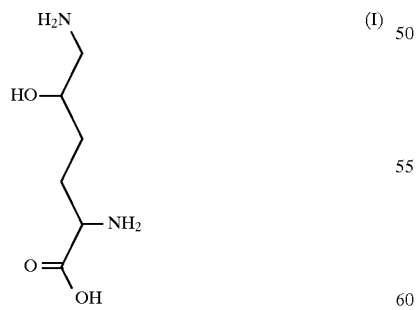

with 9-fluorenylmethyl chloroformate to provide an amino-protecting group, —Fmoc, and then reacting the amino-protected compound with diazomethane to provide a carboxyl-protecting group, —CH$_3$, to give a compound of the formula II

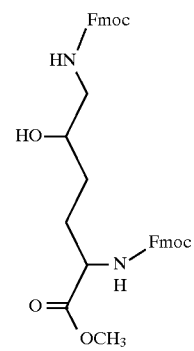

(b) reacting the compound of the formula II above with a compound of the formula III

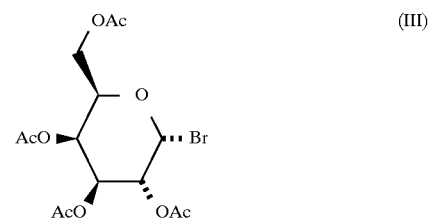

to give a compound of the formula IV

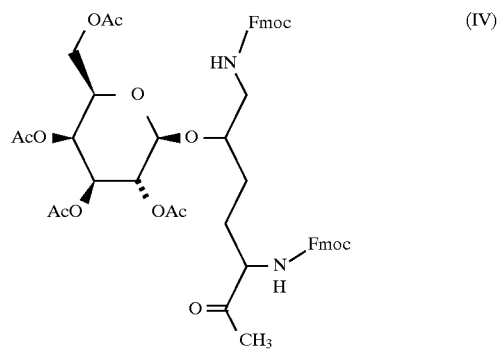

(c) reacting the compound of the formula IV with piperidine to remove the amino-protecting groups, —Fmoc, and replace them with H; with NaOH to remove the carboxyl-protecting group, —CH$_3$, and replace it with H; and with NaOH to remove the hydroxyl-protecting groups, —Ac; to give galactosylhydroxylysine (V)

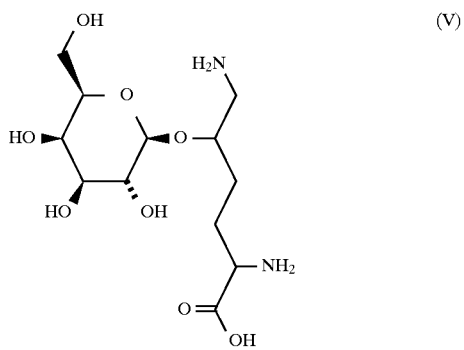

* * * * *

UNITED STATES PATENT AND TRADEMARK OFFICE
CERTIFICATE OF CORRECTION

PATENT NO. : 5,824,786
DATED : October 20, 1998
INVENTOR(S) : Chaim Manor et al.

It is certified that error appears in the above-identified patent and that said Letters Patent is hereby corrected as shown below:

Column 12, line 26, replace "Dulvecco's" with --Dulbecco's--.

Signed and Sealed this

Fifteenth Day of August, 2000

Attest:

Q. TODD DICKINSON

*Attesting Officer*     *Director of Patents and Trademarks*